BEST AVAILABLE COPY

United States Patent [19]

Ryan

[11] Plant 4,720

[45] May 19, 1981

[54] IMPATIENS PLANT NAMED PENOBSCOT

[76] Inventor: John J. Ryan, 39877 Sundale Dr., Fremont, Calif. 94538

[21] Appl. No.: 144,162

[22] Filed: Apr. 28, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—James R. Cypher

[57] ABSTRACT

This invention relates to a new and distinct variety of New Guinea Impatiens plant, known by the cultivar name Penobscot, a seedling resulting from the cross pollenation of unpatented pollen parent 77-273-1 and patented pistil parent "Mohawk" (U.S. Plant Pat. No. 4,427) and is distinguished by its medium-sized lavender flower, dark green, non-variegated foliage and pronounced spreading growth habit.

1 Drawing Figure

BACKGROUND OF THE INVENTION

The present new variety (seedling) was discovered by me in a commercial greenhouse in Fremont, Calif., as a result of a definite breeding program to produce improved and different commercial varieties of plants.

The cross pollenation of patented pistil parent Mohawk, U.S. Plant Pat. No. 4,427, granted June 12, 1979 and unpatented pollen parent 77-273-1, produced the distinct new variety herein described and selected for propagation by cuttings. Repeated propagations and flowerings of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Penobscot would be closest in characteristics is its pistil parent, Mohawk, but Penobscot is distinctly different than Mohawk in the following three characteristics:

1. The flower color of Penobscot can be described as "lavender" in comparison to Mohawk which is red-purple.

2. The foliage of Penobscot is a much darker green than that of Mohawk.

3. Penobscot has a pronounced spreading growth habit and is the most spreading plant of all the Impatiens plants that I have invented (The American Indian Series) to date.

DESCRIPTION OF PHOTOGRAPH

The accompanying color photograph illustrates the overall appearance and form of the plant as well as the nature and color of its flowers and foliage; the color rendition being as nearly true as is reasonably possible to obtain by conventional photographic procedures. The photograph was taken under intensive light conditions. Under less intensive light, the flower color is slightly darker. The photograph illustrates the pronounced spreading habit of the plant which can have branches growing out at a 20° or 30° angle to the surface of the soil.

DETAILED DESCRIPTION

Referring to the botanical details of my new variety, the following detailed description is based on observations made on Aug. 10, 1979. All plants were grown under normal environmental conditions in greenhouses. Color readings were taken during daylight hours in full sun, and all colors are based on the Royal Horticultural Society Colour Chart.

I. Plant:

*Name.*—Penobscot.

*Origin.*—Seedling of the cross pollenation of the pistil parent Mohawk 77-342-3, U.S. Plant Pat. No. 4,427 granted June 12, 1979 and the unpatented pollen parent 77-273-1.

*Form.*—Spreading, even to growing down the side of the pot in some cases.

*Height to flowering.*—25 cm.

*Growth.*—Fast.

*Type of cutting.*—Terminal or stem.

*Rooting time.*—Typical, 10–14 days.

*Rooting habit.*—Fast, dendritic.

II. Foliage:

*Arrangement.*—Lower leaves of any break opposite (usually one set); upper foliage of any break whorls of 3 to 5.

*Shape.*—Lanceolate to elliptical.

*Tip.*—Acuminate.

*Base.*—Attenuate.

*Margin.*—Serrulate.

*Veination.*—Pinnate.

*Size.*—Blades and petiole 7.5 cm to 12.5 cm; Length of blade 7 cm to 11 cm; width at widest point 3 cm to 5 cm.

*Surface.*—Glabrous.

*Variegation.*—None.

*Color.*—1. Petiole—a. Upper 182A at edge to 182D at center. b. Lower 184B 2. Veins—128A at edge to 182D at center. a. Lower 183C 3. Leaf—a. Upper 147A to 147B b. Lower 183D.

III. Stem:

*Color.*—In new growth fairly red (184A-B) losing some color with age.

*Internode.*—1. Length—Short to moderate. 2. Size—Less than average.

*Node expanded (relative to internode).*—Larger than internode.

BEST AVAILABLE COPY

*Breaking action.*—Very good.

IV. Flower:

*Form.*—Typical with some notching especially on the top petal.

*Borne.*—End of branches, terminal.

*Blooming habit.*—1. Relative number—Many. 2. Time to flowering—Short. 3. Longevity—Typical 3-5 days.

*Size of mature flower.*—First flower on a plant may be small. 1. Length—5 cm to 6 cm. 2. Width—5 cm to 6.5 cm. 3. Spur—5.5 cm to 6 cm.

*Color.*—Lighter lavender under high light and heat.

| | |
|---|---|
| 1. Eye—67A<br>2. Middle: 68A<br>3. Edge—67A-67B | Candy stripes 67A-67B |
| 4. Pedicel—145B | |

V. Reproductive organs:

*Stamen.*—

| | |
|---|---|
| 1. Anthers<br>2. Filaments | Typical, fused hood over pistil |
| 3. Pollen<br>a. Color—158B<br>b. Abundance—Little less than average | |

*Pistils.*—

| | |
|---|---|
| 1. Style<br>2. Ovaries | Typical, but colored 59A to 59B |

I claim:

1. A new and distinct form of impatients plant as described and illustrated, known by the cultivar name Penobscot.

* * * * *

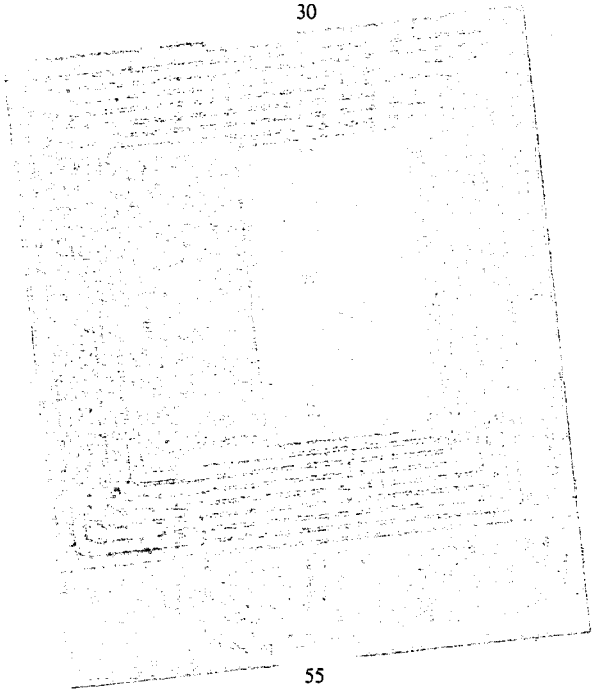

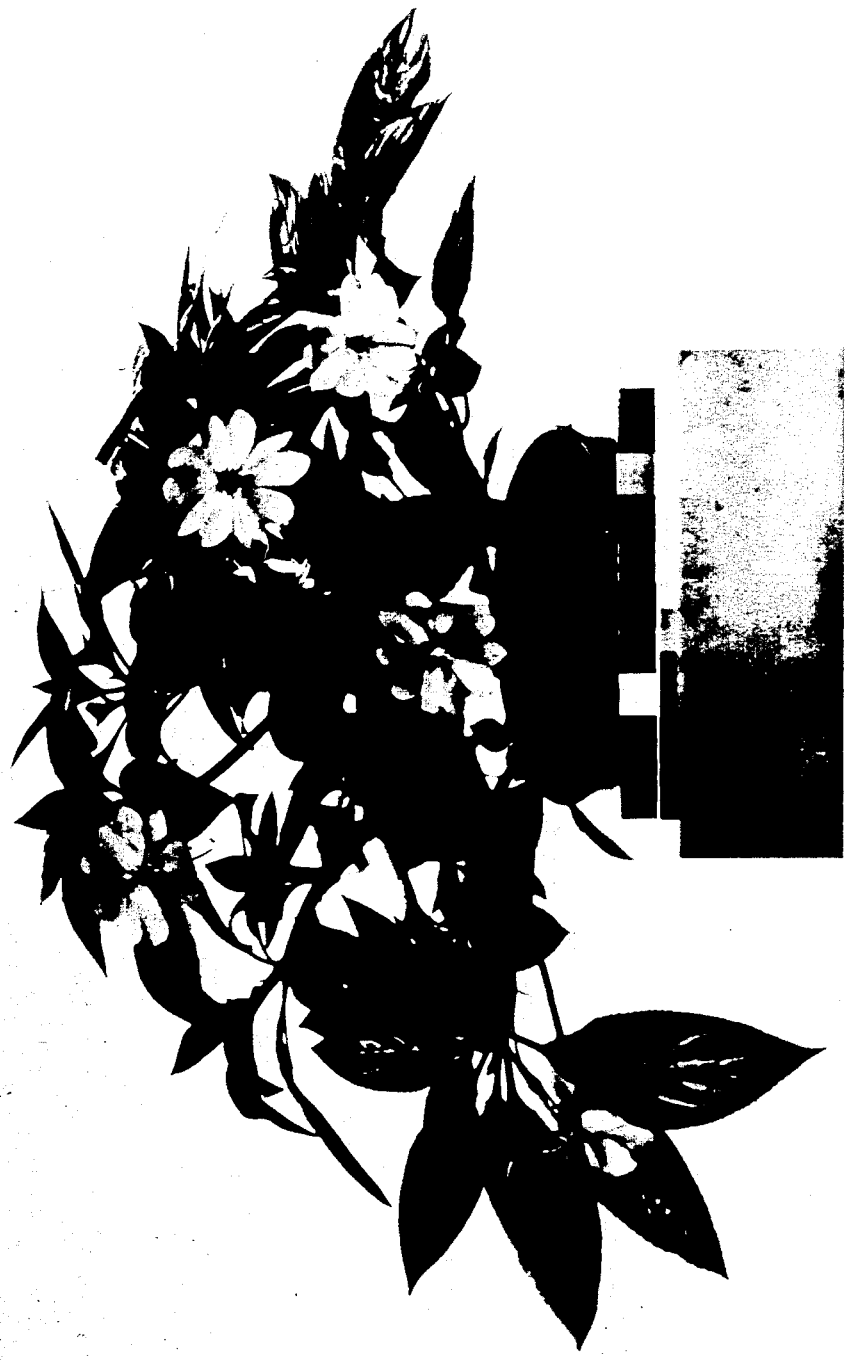

PLT 67.8 SR
H9898 OR PP 4,720
BEST AVAILABLE COPY